United States Patent [19]

Lockyer, Jr. et al.

[11] 4,187,386
[45] Feb. 5, 1980

[54] CYCLIZATION OF 1,5-HEXADIENE TO CYCLOHEXENE

[75] Inventors: George D. Lockyer, Jr., Snyder; Dennis E. Burd, Kenmore; Richard F. Sweeney, Elma; Bernard Sukornick, Williamsville, all of N.Y.; Harry E. Ulmer, Morristown, N.J.

[73] Assignee: Allied Chemical Corporation, Morris Township, Morris County, N.J.

[21] Appl. No.: 974,397

[22] Filed: Dec. 29, 1978

[51] Int. Cl.$^2$ .............................................. C07C 13/20
[52] U.S. Cl. ...................................... 585/367; 585/369
[58] Field of Search ................................ 585/367, 369

[56] References Cited

U.S. PATENT DOCUMENTS

| | | | |
|---|---|---|---|
| 3,247,270 | 4/1966 | Kirk | 585/369 |
| 3,507,927 | 4/1970 | Olechowski et al. | 585/367 |
| 3,510,533 | 5/1970 | Maxfield | 585/369 |
| 3,655,791 | 4/1972 | De Young | 585/367 |
| 3,691,253 | 9/1972 | Hughes | 585/367 |

OTHER PUBLICATIONS

M. Julia et al., Bull. Soc. Chim., Fr., 2397, 1966.
M. Julia et al., Bull. Soc. Chim., Fr., 1796, 1973.
I. Tabushi et al., Tet. Letters, 2487, 1966.

*Primary Examiner*—Veronica O'Keefe
*Attorney, Agent, or Firm*—Jay P. Friedenson

[57] ABSTRACT

1,5-Hexadiene is cyclized to cyclohexene by contacting 1,5-hexadiene with a mixture of a first catalyst selected from the group consisting of chromium oxides, chromium chlorides, chromium bromides, molybdenum oxides, molybdenum chlorides, molybdenum bromides, tungsten oxides, tungsten chlorides, tungsten bromides, iron oxides, cobalt oxides, nickel oxides, elemental sulfur, $SiO_2$, $Al_2O_3$, vanadium metal, vanadium oxides, $VOF_3$, and mixtures thereof, and a second catalyst selected from a tin (IV) halide and mixtures thereof.

19 Claims, No Drawings

CYCLIZATION OF 1,5-HEXADIENE TO CYCLOHEXENE

BACKGROUND OF THE INVENTION

Cyclohexane is a known compound which is an important intermediate or building block for other commercially important chemicals. For example, it is used as a monomer or comonomer for a variety of polymerization reactions and it is used as an intermediate in the manufacture of cyclohexanone.

It is an object of this invention to provide a new route to cyclohexene.

Other objects and advantages of the invention will become apparent from the following description.

SUMMARY OF THE INVENTION

It has been found that cyclohexene may be prepared by the cyclization of 1,5-hexadiene. This has been accomplished by contacting 1,5-hexadiene with a mixture of a first catalyst selected from the group consisting of chromium oxides, chromium chlorides, chromium bromides, molybdenum oxides, molybdenum chlorides, molybdenum bromides, tungsten oxides, tungsten chlorides, tungsten bromides, iron oxides, cobalt oxides, nickel oxides, elemental sulfur, $SiO_2$, $Al_2O_3$, vanadium metal, vanadium oxides, $VOF_3$, and mixtures thereof, and a second catalyst selected from a tin (IV) halide and mixtures thereof.

DETAILED DESCRIPTION OF THE INVENTION AND OF THE PREFERRED EMBODIMENTS

The first catalyst may be any of the materials described in any valence state. For example, chromium oxides include $CrO_3$ and $Cr_2O_3$; cobalt oxides include $CoO$ and $Co_3O_4$ and vanadium oxides include $V_2O_5$, $V_2O_4$ and $V_2O_3$.

The first catalyst may be used alone but it is preferably used in conjunction with a support. The support need not be inert provided that no reactions deleterious to the desired reaction take place. This may readily be ascertained by one of ordinary skill in the art. The support may also be catalytically active for the subject cyclization reaction. Alumina ($Al_2O_3$), silica ($SiO_2$), aluminum fluoride ($AlF_3$), sodium magnesium fluoride ($NaMgF$), aluminosilicates and carbon are examples of suitable supports. Of these supports, alumina and silica are named catalytic materials herein. The preferred support ia alumina. Other suitable support materials will readily occur to those skilled in the art.

The amount of the first catalyst is not critical. As little as 0.1 weight % based on the hexadiene starting material may be employed. Large excesses will not deleteriously affect the reaction, but economic considerations will govern.

Generally from about 0.1–100 weight % based on the hexadiene starting material may be employed with the preferred range being in the order of about 5–15 weight.

If a support is employed, the weight % based on the first catalyst should generally be in the range of about 0.1–75. Preferably, the weight % of the support to the first catalyst should be from about 10 to 30.

The tin (IV) halide second catalyst may be any of $SnF_4$ $SnCl_4$, $SnBr_4$ or $SnI_4$. Preferably the tin (IV) halide is one in which the halide has an atomic weight over 19 (i.e., $SnCl_4$, $SnBr_4$ or $SnI_4$).

$SnF_4$ is generally insoluble so that if this is selected as the tin (IV) halide, it should be employed in connection with an inert support as described herein. The amount of the tin (IV) halide second catalyst is not critical. As little as 0.1 weight % based on the hexadiene starting material may be employed. As in the case of the first catalyst, large amounts will not deleteriously affect the reaction, but economic considerations govern. Generally, from about 0.1–50 weight % based on the hexadiene starting material should be employed with the preferred range being from about 5–20 weight %.

The tin (IV) halide (second catalyst) should be admixed with the first catalyst so that the 1,5-hexadiene reactant contacts both catalytic components during the cyclization reaction. This may be accomplished by stirring or other form of agitation or by any other method which may occur to those or ordinary skill in the art.

An inert, non-polar solvent may sometimes be used to advantage. This is particularly the case when the tin (IV) halide chosen is a salt, such as $SnBr_4$ or $SnI_4$.

Generally it has been found that when such a solvent is employed, yields of the cyclohexene product increase, but conversions decrease. If a solvent is employed it should be inert to the 1,5-hexadiene reactant, the cyclohexene product and the first and second catalysts. Aliphatic hydrocarbon solvents are particularly suitable, especially the $C_5$–$C_{20}$ aliphatic hydrocarbon solvents of which n-pentane, n-heptane, n-dodecane and n-eicosane are illustrative.

Temperatures are not critical. The reaction proceeds readily at room temperature as well as elevated temperatures. Generally, temperatures above about 170° C. should be avoided since above 170° C. product yields will be diminished due to polymerization reactions.

Likewise, contact time is not critical. Good yields are obtained within a short period of time. Long contact times will not generally deleteriously affect the reaction unless temperatures are unduly high. Usually, yields and conversions are optimized within about 1–3 hours.

Recovery of the cyclohexene product is simple and efficient. The tin (IV) halide is extracted from the product mixture such as with dilute aqueous HCl, followed by neutralization such as with $NaHCO_3$ and drying such as with $K_2CO_3$. The resulting product mixture is then subjected to distillation. A pure form of cyclohexene is recovered.

In the following examples, parts and percentages are on a weight basis and temperatures are in degrees Centigrade.

EXAMPLE 1

A catalyst composed of 20% chromia ($Cr_2O_3$) on alumina was prepared by precipitating chromium (III) nitrate of alumina (20/60 mesh) and calcining at 600° C. for 5 days. To a 3 oz. Fisher-Porter aerosol compatability tube (modified so that the reaction mixture contacts only glass and fluoropolymer) was added 1.5 grams of the $Cr_2O_3/Al_2O_3$ catalyst so prepared, 20.0 ml of 1,5-hexadiene, 20.0 ml. of dodecane, 2.26 g. of $SnCl_4$ and 1.00 ml. of n-heptane. The tube was sealed, heated to 60° C. and maintained at that temperature for 96 hours with vigorous shaking. The resulting product mixture was extracted with dilute aqueous HCl (10%) followed by neutralization with $NaHCO_3$ and drying with anhydrous $K_2CO_3$. Gas chromatographic analysis revealed a 17% yield of cyclohexene product (b.p. 83°–84° C.) with a 5.1% conversion of 1,5-hexadiene. By-products observed were 5-chloro-1-hexene (10%) and oligomeric products (72%). Product identities were confirmed by infrared analysis.

EXAMPLE 2

The process of Example 1 was repeated but with heating at 80° C. rather than 60° C. An 8.4% 1,5-hexadiene conversion was obtained to the following product mix:

| cyclohexene | 14% |
| 5-chloro-1-hexene | 11% |
| 1,4-hexadiene | 11% |
| 2,4-hexadiene | 1% |
| oligomeric products | 63% |

EXAMPLE 3

The process of Example 2 was repeated except that the dodecane solvent was omitted and the sealed tube was heated to 150° C. for 2 hours. Upon work-up, an 8.5% conversion of 1,5-hexadiene was obtained to the following product mix:

| cyclohexene | 8% |
| 5-chloro-1-hexene | 16% |
| 1,4-hexadiene | 14% |
| 2,4-hexadiene | 1% |
| oligomeric products | 61% |

EXAMPLE 4

The process of Example 3 was repeated except that heating was conducted at 120° C. for a period of 6 hours and 3.0 grams of $Cr_2O_3/Al_2O_3$ were employed. Conversion of 1,5-hexadiene was 15% to the following product mix:

| cyclohexene | 7% |
| 5-chloro-1-hexene | 8% |
| 1,4-hexadiene | 7% |
| 2,4-hexadiene | 1% |
| oligomeric products | 78% |

EXAMPLE 5

To a 3 oz. Fisher-Porter tube was added 1.5 grams $MoO_3$, 20.0 ml 1,5-hexadiene, 2.26 grams $SnCl_4$ and 1.00 ml n-heptane. The tube was sealed and heated to 50° C. for 17 hours with vigorous shaking. Upon work-up, a 13% conversion of 1,5-hexadiene was obtained to the following product mix:

| cyclohexene | 2% |
| 5-chloro-1-hexene | 15% |
| 1,4-hexadiene | 12% |
| oligomeric products | 70% |

Product identities were confirmed by infrared analysis

EXAMPLE 6

The process of Example 5 was repeated except that $Fe_2O_3$ was used in place of $MoO_3$. A 4.1% conversion of 1,5-hexadiene was obtained to the following product mix:

| cyclohexene | 2% |
| 5-chloro-1-hexene | 29% |
| 1,4-hexadiene | 29% |
| oligomeric products | 40% |

EXAMPLE 7

The process of Example 3 was repeated except that 3.7 grams of $SnBr_4$ were employed instead of the $SnCl_4$. The observed conversion of 1,5-hexadiene was 4.3% to the following product mix:

| cyclohexene | 1% |
| 5-bromo-1-hexene | <1% |
| 1,4-hexadiene | <1% |
| oligomeric products | 98% |

EXAMPLE 8

The process of Example 7 was repeated except that 5.3 grams of $SnI_4$ were employed in place of the $SnBr_4$. The The observed conversion of 1,5-hexadiene was 4.8% to the following product mix:

| cyclohexene | <1% |
| 1,4-hexadiene | 12% |
| 2,4-hexadiene | <1% |
| oligomeric products | 86% |

EXAMPLES 9-20

The process of Example 1 was repeated except that the first catalyst, reaction times and reaction temperatures were varied as shown in Table I. The conversions of 1,5-hexadiene and the cyclohexene yields obtained are shown in the table:

TABLE I

| Example | First Catalyst | Reaction Time (hrs.) | Reaction Temp. (°C.) | Conversion of 1,5-hexadiene (%) | Cyclohexane yield (%) |
|---|---|---|---|---|---|
| 9 | $MoCl_5$ | 17 | 150 | 26 | 0.2 |
| 10 | elemental sulfur | 17 | 150 | 52 | 0.4 |
| 11 | $SiO_2$ | 17 | 150 | 18 | 0.9 |
| 12 | $Al_2O_3$ | 2 | 150 | 34 | 1.6 |
| 13 | $WCl_6$ | 17 | 150 | 24 | 0.7 |
| 14 | $V_2O_5$ | 17 | 150 | 17 | 0.3 |
| 15 | $V_2O_4$ | 17 | 150 | 19 | 0.1 |
| 16 | $V_2O_3$ | 17 | 150 | 11 | 2.4 |
| 17 | V (metal) | 17 | 150 | 6.4 | 1.2 |
| 18 | V (metal) | 17 | 170 | 27 | 0.4 |
| 19 | $VOF_3$ | 17 | 150 | 55 | 0.7 |
| 20 | 20% $Cr_2O_3$/ 80% $Al_2O_3$/ 20 ml $C_{12}H_{26}$ | 17 | 25 | 0.6 | 41 |

EXAMPLES 21-27

The process of Example 1 is repeated with the first and second catalysts shown in Table II. In all cases cyclohexene is produced.

TABLE II

| Example | First Catalyst | Second Catalyst |
|---|---|---|
| 21 | $CrCl_3$ | $SnI_4$ |
| 22 | $CrBr_3$ | $SnBr_4$ |
| 23 | $MoBr_5$ | $SnCl_4$ |

TABLE II-continued

| Example | First Catalyst | Second Catalyst |
|---|---|---|
| 24 | W$_2$O$_3$ | SnF$_4$* |
| 25 | WBr$_6$ | SnI$_4$ |
| 26 | CoO | SnCl$_4$ |
| 27 | NiO | SnCl$_4$ |

*10% Cr$_2$O$_3$ support based on the first catalyst is employed in lieu of the hydrocarbon solvent.

We claim:

1. The method for the production of cyclohexene which comprises contacting, 1,5-hexadiene with a mixture of a first catalyst selected from the group consisting of chromium oxides, chromium chlorides, chromium bromides, molybdenum oxides, molybdenum chlorides, molybdenum bromides, tungsten oxides, tungsten chlorides, tungsten bromides, iron oxides, cobalt oxides, nickel oxides, elemental sulfur, SiO$_2$, Al$_2$O$_3$, vanadium metal, vanadium oxides and VOF$_3$, and mixtures thereof, and a second catalyst selected from a tin (IV) halide and mixtures thereof.

2. The method according to claim 1 in which the contacting is carried out with agitation.

3. The method according to claim 1 in which the contacting is carried out in the presence of an aliphatic hydrocarbon.

4. The method according to claim 1 in which the tin (IV) halides is SnF$_4$ supported on an inert support.

5. The method according to claim 1 in which the halide in the tin (IV) halide has an atomic weight over 19.

6. The method according to claim 1 in which the first catalyst is selected from the group consisting of chromium oxides, molybdenum oxides, molybdenum halides, tungsten halides, iron oxides, elemental sulfur, SiO$_2$, Al$_2$O$_3$, vanadium metal, vanadium oxides, VOF$_3$ and mixtures thereof.

7. The method according to claim 6 in which the halide in the tin (IV) halide has an atomic weight over 19.

8. The method according to claim 7 in which the contacting is carried out in the presence of an aliphatic hydrocarbon solvent.

9. The method according to claim 8 in which the tin (IV) halide is SnCl$_4$ and in which the contacting is carried out with agitation.

10. The method according to claim 1 in which the first catalyst is selected from the group consisting of Cr$_2$O$_3$, MoO$_3$, Fe$_2$O$_3$, MoCl$_5$, elemental sulfur, SiO$_2$, Al$_2$O$_3$, WCl$_6$, V$_2$O$_5$, V$_2$O$_4$, V$_2$O$_3$, vanadium metal, VOF$_3$ and mixtures thereof.

11. The method according to claim 2 in which the halide in the tin (IV) halide has an atomic weight over 19.

12. The method according to claim 11 in which the contacting is carried out in the presence of an aliphatic hydrocarbon solvent.

13. The method according to claim 12 in which the tin (IV) halide is SnCl$_4$.

14. The method according to claim 13 in which the contacting is carried out with agitation.

15. The method according to claim 12 in which the first catalyst is Cr$_2$O$_3$.

16. The method according to claim 12 in which the first catalyst is a mixture of Cr$_2$O$_3$ and Al$_2$O$_3$.

17. The method according to claim 16 in which the tin (IV) halide is SnCl$_4$.

18. The method according to claim 17 in which the contacting is carried out with agitation.

19. The method according to claim 18 in which the solvent is n-dodecane.

* * * * *